(12) United States Patent
Edamatsu (10) Patent No.: US 9,492,641 B2
(45) Date of Patent: Nov. 15, 2016

(54) GUIDEWIRE

(71) Applicant: ASAHI INTECC CO. LTD., Nagoya-shi, Aichi (JP)

(72) Inventor: Motonari Edamatsu, Seto (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 216 days.

(21) Appl. No.: 13/868,643

(22) Filed: Apr. 23, 2013

(65) Prior Publication Data

US 2013/0289445 A1 Oct. 31, 2013

(30) Foreign Application Priority Data

Apr. 26, 2012 (JP) ................. 2012-101305

(51) Int. Cl.
*A61M 25/09* (2006.01)
*A61M 25/00* (2006.01)

(52) U.S. Cl.
CPC ......... *A61M 25/09* (2013.01); *A61M 25/0041* (2013.01); *A61M 2025/09083* (2013.01); *A61M 2025/09108* (2013.01); *A61M 2025/09175* (2013.01)

(58) Field of Classification Search
None
See application file for complete search history.

(56) References Cited

U.S. PATENT DOCUMENTS

| | | | |
|---|---|---|---|
| 4,676,249 A * | 6/1987 | Arenas et al. | 600/434 |
| 4,846,186 A * | 7/1989 | Box et al. | 600/434 |
| 4,886,067 A * | 12/1989 | Palermo | 600/434 |
| 4,917,104 A | 4/1990 | Rebell | |
| 4,932,419 A | 6/1990 | de Toledo | |
| 5,060,660 A | 10/1991 | Gambale et al. | |
| 5,174,302 A * | 12/1992 | Palmer | 600/585 |
| 5,345,945 A * | 9/1994 | Hodgson et al. | 600/585 |
| 6,146,339 A | 11/2000 | Biagtan et al. | |
| 2005/0027212 A1 | 2/2005 | Segner et al. | |
| 2007/0083132 A1 | 4/2007 | Sharrow | |
| 2010/0318065 A1* | 12/2010 | Miyata et al. | 604/526 |
| 2011/0160705 A1 | 6/2011 | Matsumoto et al. | |

(Continued)

FOREIGN PATENT DOCUMENTS

EP 0 739 641 10/1996
EP 2 263 735 A1 12/2010

(Continued)

OTHER PUBLICATIONS

May 24, 2013 Search Report issued in European Patent Application No. 13 16 3338.

(Continued)

*Primary Examiner* — Devin Henson
*Assistant Examiner* — Matthew Kremer
(74) *Attorney, Agent, or Firm* — Oliff PLC (57) ABSTRACT

A guidewire includes a core shaft including a distal end portion and a proximal end portion, an outer coil disposed so as to cover the distal end portion, and an inner coil disposed inside of the outer coil. The outer coil includes a first bent portion that is bent at a first angle in a first direction. The inner coil includes a second bent portion that is bent at a second angle in the first direction. The second angle is larger than the first angle.

5 Claims, 5 Drawing Sheets

(56) References Cited

U.S. PATENT DOCUMENTS

2011/0319923 A1* 12/2011 Watanabe et al. ............ 606/192
2012/0029476 A1    2/2012 Kanazawa

FOREIGN PATENT DOCUMENTS

| EP | 2 415 497 A1 | 2/2012 |
| EP | 2 417 999 A1 | 2/2012 |
| JP | A-05-042225 | 2/1993 |
| JP | 2011-147752 | 8/2011 |
| JP | 2012-29978 A | 2/2012 |
| WO | WO 2010/078335 | 7/2010 |

OTHER PUBLICATIONS

Jun. 3, 2015 Chinese Office Action issued in Chinese Application No. 201310116768.0.

Apr. 8, 2015 OA in Japanese Patent Application No. 2012-101305.

\* cited by examiner

GUIDEWIRE

CROSS-REFERENCE TO RELATED APPLICATION

This application claims priority to Japanese Patent Application No. 2012-101305 filed with the Japanese Patent Office on Apr. 26, 2012, the entirety of which is hereby incorporated by reference.

BACKGROUND OF THE INVENTION

1. Field of the Invention

The disclosed embodiments relate to a medical device. More specifically, the disclosed embodiments relate to a guidewire.

2. Description of Related Art

A guidewire is a known example of a medical device that is used for medical treatment in a blood vessel, such as percutaneous transluminal coronary angioplasty. A guidewire is used to guide a device, such as a balloon or a stent, to a lesion.

For example, Japanese Unexamined Patent Application Publication No. 5-42225, International Publication No. 2010/078335, and U.S. Pat. No. 4,917,104 each describe a guidewire including a core shaft that includes a distal end portion and a proximal end portion and a coil that covers an outer periphery of the core shaft. The guidewire is configured so that a distal end portion (distal portion) of the guidewire can be bent in a predetermined direction. In general, a distal end portion of a core shaft corresponds to a distal portion of a guidewire, and a proximal end portion of the core shaft corresponds to a proximal portion of the guidewire. A distal portion of a guidewire is inserted into a human body, and a proximal portion of the guidewire is operated by an operator, such as a doctor.

To be specific, the guidewire described in Japanese Unexamined Patent Application Publication No. 5-42225 includes a core shaft including a distal end portion and a proximal end portion, an inner coil that covers an outer periphery of the distal end portion, an outer coil that covers an outer periphery of the inner coil, and a pull wire. One end of the pull wire is connected to a distal end of the outer coil and the other end of the pull wire extends to the proximal end portion of the core shaft, and the pull wire is configured so that an operator can pull the pull wire. With the guidewire described in Japanese Unexamined Patent Application Publication No. 5-42225, a distal portion of the guidewire, which has a linear shape, can be bent by pulling the pull wire in the proximal direction.

Each of the guidewires described in International Publication No. 2010/078335 and U.S. Pat. No. 4,917,104 includes a core shaft that includes a distal end portion that has been bent beforehand and a coil that covers an outer periphery of the distal end portion of the core shaft along the bent shape of the distal end portion. A distal portion of the guidewire is bent in a predetermined direction.

U.S. Patent Application Publication No. 2005/0027212 describes a guidewire including a distal portion that is not bent and has a linear shape.

SUMMARY

In contrast to the guidewire described in U.S. Patent Application Publication No. 2005/0027212, which includes a distal portion having a linear shape, each of the guidewires described in Japanese Unexamined Patent Application Publication No. 5-42225, International Publication No. 2010/078335, and U.S. Pat. No. 4,917,104 includes a distal portion that can be bent by pulling a pull wire or a distal portion that has been bent beforehand. Because the distal portion of the guidewire is bent, an operator can selectively insert the guidewire into a target blood vessel. To be more specific, with each of the guidewires described in Japanese Unexamined Patent Application Publication No. 5-42225, International Publication No. 2010/078335, and U.S. Pat. No. 4,917,104, an operator can selectively insert the guidewire into a branch vessel that branches at a comparatively large obtuse angle from a trunk vessel into which the guidewire has been inserted (hereinafter, referred to as an "obtuse-angle branch vessel") by decreasing the bending angle of the distal portion. Moreover, an operator can selectively insert the guidewire into a branch vessel that branches at an angle of about 90° or a comparatively small acute angle from a trunk blood vessel into which the guidewire has been inserted (hereinafter, referred to as an "acute-angle branch vessel") by increasing the bending angle of the distal portion. In particular, there are many acute-angle branch vessels in a brain, a liver, and the like.

However, existing guidewires have a problem in that it is necessary to frequently change the bending angle of the distal portion in accordance with the curvature of the blood vessel. Moreover, selectivity in selecting an acute-angle branch vessel is not significantly improved even when the bending angle of the distal portion is increased. Therefore, there is a demand for a guidewire having high selectivity in selecting not only an obtuse-angle branch vessel but also an acute-angle branch vessel.

According to an aspect of the present invention, a guidewire includes a core shaft including a distal end portion and a proximal end portion, an outer coil disposed so as to cover the distal end portion, and an inner coil disposed inside of the outer coil. The outer coil includes a first bent portion that is bent at a first angle in a first direction. The inner coil includes a second bent portion that is bent at a second angle in the first direction. The second angle is larger than the first angle.

In the present specification, the term "first direction" refers to a direction that is perpendicular to the longitudinal direction of the guidewire (that is, a radial direction of the guidewire). The term "first angle" refers to an acute angle (α) between an imaginary line (A) that extends along a first distal end section (21) that is located on the distal side of the first bent portion (22) and an imaginary line (B) that extends along a first proximal end section (23) that is located on the proximal side of the first bent portion (22). The term "second angle" refers to an acute angle (β) between an imaginary line (C) that extends along a second distal end section (31) that is located on the distal side of the second bent portion (32) and an imaginary line (D) that extends along the second proximal end section (33) that is located on the proximal side of the second bent portion (32). Here, the numerals in the parentheses correspond to those in FIG. 1B.

DETAILED DESCRIPTION OF EMBODIMENTS

Hereinafter, the structure and the advantageous effects of a guidewire according to a first embodiment of the present invention will be described with reference to the drawings. The guidewire is only partially illustrated in the drawings.

Figure 1A:
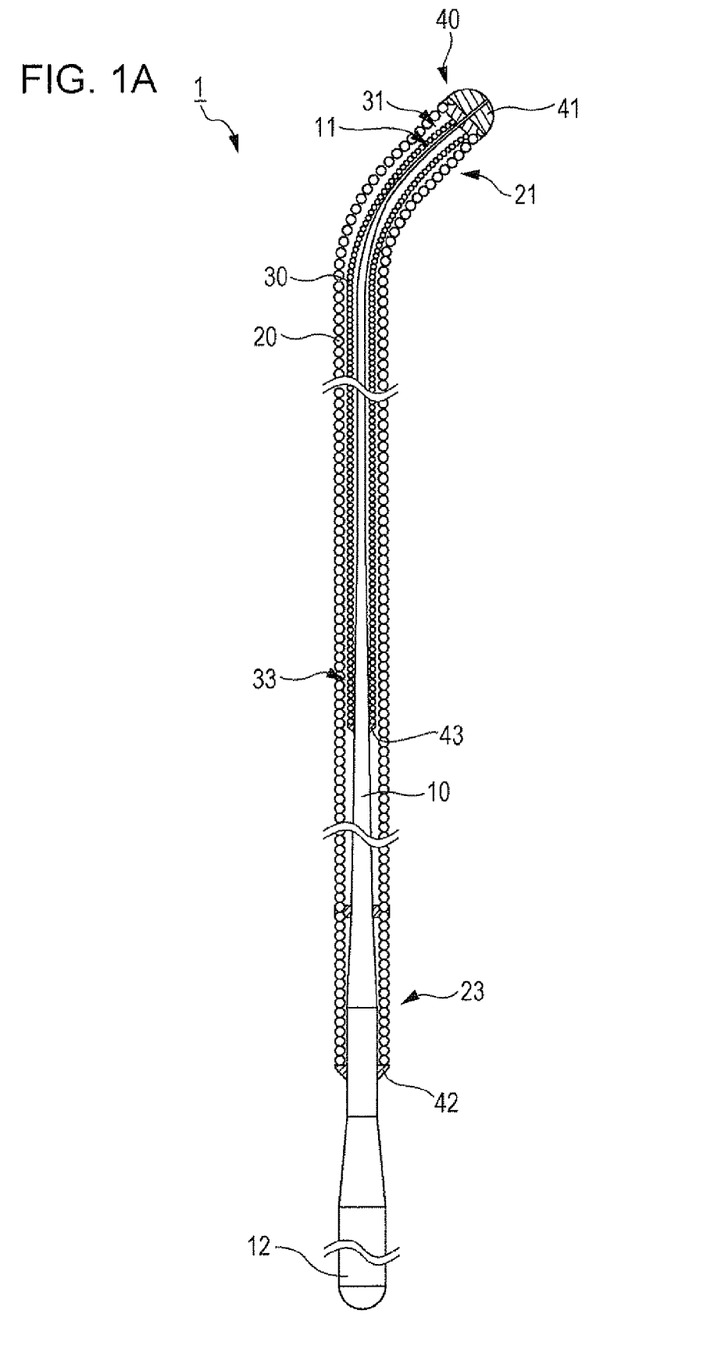
FIG. 1A is a schematic longitudinal sectional view of a guidewire according to a first embodiment of the present invention.
Figure 1B:
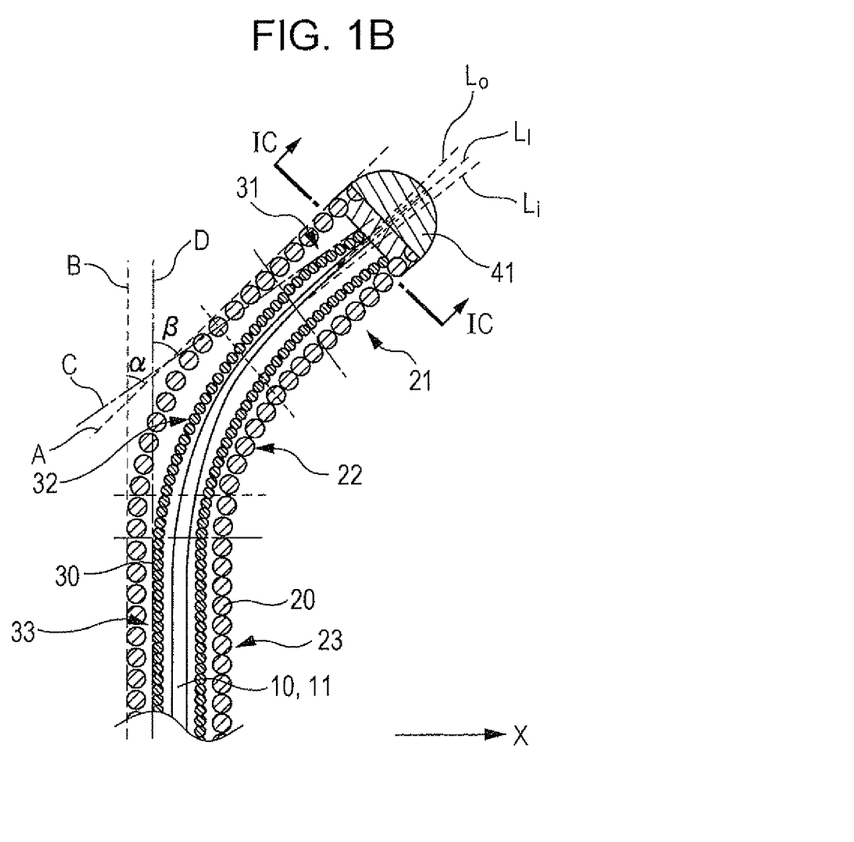
FIG. 1B is an enlarged view of a distal portion of the guidewire illustrated in FIG. 1A.
Figure 1C:
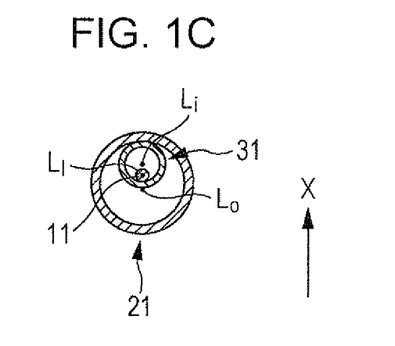
FIG. 1C is a cross-sectional view of the guidewire taken along line IC-IC of FIG. 1B.

FIGS. 1A to 1C illustrate a guidewire 1 according to the first embodiment of the present invention. The guidewire 1 includes a core shaft 10 including a distal end portion 11 and a proximal end portion 12, an outer coil 20 that is disposed so as to cover the distal end portion 11, and an inner coil 30 disposed inside of the outer coil 20.

The core shaft 10, which includes the distal end portion 11 and the proximal end portion 12, is a cylindrical member that tapers from the proximal end portion 12 toward the distal end portion 11 and becomes more flexible toward the distal end portion 11. A tip portion of the distal end portion 11 of the core shaft 10 may be press-formed so as to have a flat plate-like shape. When the tip portion of the distal end portion 11 has a flat plate-like shape, the tip portion is more flexible than in a case where the tip portion has a cylindrical shape.

The core shaft 10 may be made of, for example, a stainless steel, a super elastic alloy such as a Ni—Ti alloy, a piano wire, or a tungsten wire. Examples of stainless steel include a martensitic stainless steel, a ferritic stainless steel, an austenitic stainless steel, an austenite, a ferritic duplex stainless steel, and a precipitation hardening stainless steel. Among these, an austenitic stainless steel is preferable, and in particular, SUS304, SUS316, or SUS316L is more preferable.

The outer coil 20 forms the outer shape of a distal portion of the guidewire 1. The outer coil 20 is a cylindrical member that is made by helically winding a single wire or by stranding a plurality of wires. The outer coil 20 is flexible and elastic. To be specific, the outer coil 20 includes a first distal end section 21, a first bent portion 22, and a first proximal end section 23. The first distal end section 21 has a linear shape. The first bent portion 22 is bent at a first angle α in a first direction X and is connected to the first distal end section 21. The first proximal end section 23 has a linear shape and is connected to the first bent portion 22. Therefore, when a load is applied to the outer coil 20 in a direction from the first distal end section 21 toward the first proximal end section 23, the first bent portion 22 can be easily bent in the first direction X.

Because the outer coil 20 forms the outer shape of the distal portion of the guidewire 1, the first angle α is the bending angle of the bent portion of the guidewire 1. It is preferable that the first angle α be in the range of 5° to 90°. This is because, when the first angle α is in the range of 5° to 90°, it is easy to selectively insert the guidewire into a branch vessel. It is more preferable that the first angle α be in the range of 45° to 90° because, in this case, it becomes easier to selectively insert the guidewire into an acute-angle branch vessel. It is further preferable that the first angle α be in the range of 50° to 80°.

Examples of the material of the wire of the outer coil 20 include a stainless steel such as a martensitic stainless steel, a ferritic stainless steel, an austenitic stainless steel, an austenite, a ferritic duplex stainless steel, and a precipitation hardening stainless steel; a super elastic alloy such as a Ni—Ti alloy; and platinum, gold, tungsten, or the like, which is a radiopaque metal.

The inner coil 30 is disposed inside of the outer coil 20 (the distal portion of the guidewire 1). The inner coil 30 is a cylindrical member that is made by helically winding a single wire or by stranding a plurality of wires. The inner coil 30 is flexible and elastic. To be specific, the inner coil 30 includes a second distal end section 31, a second bent portion 32, and a second proximal end section 33. The second distal end section 31 has a linear shape. The second bent portion 32 is bent in the first direction X at a second angle β that is larger than the first angle α and is connected to the second distal end section 31. The second proximal end section 33 has a linear shape and is connected to the second bent portion 32. Therefore, when a load is applied to the inner coil 30 in a direction from the second distal end section 31 toward the second proximal end section 33, the second bent portion 32 can be easily bent in the first direction X. Because the second angle β is larger than the first angle α, the second bent portion 32 can be more easily bent in the first direction X than the first bent portion 22 of the outer coil 20.

It is preferable that the second angle β be in the range of 6° to 91°. This is because, when the second angle β is in the range of 6° to 91°, an operator can selectively insert the guidewire into a branch vessel easily, because the inner coil 30 can be more easily bent in the first direction X. It is more preferable that the second angle β be in the range of 46° to 91° because, in this case, an operator can selectively insert the guidewire into an acute-angle branch vessel more easily. It is further preferable that the second angle β be in the range of 51° to 81°.

It is preferable that the difference between the second angle β and the first angle α be in the range of 1° to 5°. This is because, in this case, as described below with reference to FIGS. 2A to 2C, when a bent end portion of the guidewire is, for example, pressed against an inner wall of an acute-angle branch vessel and a bending force is applied to the bent end portion, the bent end portion can be easily bent in accordance with the curvature of the acute-angle branch vessel.

The material of the wire of the inner coil 30 may be the same as that of the wire of the outer coil 20.

The distal end portion 11 of the core shaft 10 is inserted into the inner coil 30, and the inner coil 30 is disposed so as to cover the distal end portion 11.

As illustrated in FIG. 1C, the axis $L_i$ of the second distal end section 31 of the inner coil 30, which is located on the distal side of the second bent portion 32 (nearer to the tip portion of the guidewire 1), is displaced/offset in the first direction X from the axis $L_o$ of the first distal end section 21 of the outer coil 20, which is located on the distal side of the first bent portion 22.

The axis $L_I$ of the distal end portion 11 of the core shaft 10 is displaced/offset from the axis $L_i$ of the second distal end section 31 toward the axis $L_o$ of the first distal end section 21.

It is preferable that the inner coil 30 be a linear cylindrical member that is made by stranding a plurality of wires and the outer coil 20 be a linear cylindrical member that is made by winding a single wire. The reason for this will be described below in relation to the advantageous effects.

The outer coil 20 and the inner coil 30 are fixed to each other through a fixing unit 40. To be specific, the tip portion of the first distal end section 21 of the outer coil 20, the tip portion of the second distal end section 31 of the inner coil 30, and the tip portion of the distal end portion 11 of the core shaft 10 are fixed to one another through a distal end brazed portion 41 having a hemispherical shape.

As described below, a method of manufacturing the guidewire 1 according to the present includes a step of covering the inner coil 30, which has been bent beforehand at a large angle in the first direction X, with the outer coil 20, which has a linear shape prior to assembly of the guidewire 1. Therefore, the first bent portion 22 of the outer coil 20 is formed when the inner coil 30, which has been bent beforehand at a large angle in the first direction X, comes into contact with an inner peripheral surface of the outer coil 20, which has a linear shape prior to assembly of the guidewire 1, so as to bend the outer coil 20. That is, the inner coil 30, which is urged the first direction X, is in contact with the outer coil 20, which has a linear shape prior to assembly of the guidewire 1, and thereby the first bent portion 22 of the outer coil 20 is formed.

A proximal end of the first proximal end portion 23 of the outer coil 20 and a proximal end of the distal end portion 11 of the core shaft 10 are fixed to each other through a first proximal end brazed portion 42. A proximal end of the second proximal end portion 33 of the inner coil 30 and a middle portion of the distal end portion of the core shaft 10 are fixed to each other through a second proximal end brazed portion 43 at a position on the distal side of the first proximal end brazed portion 42.

Examples of the material of each of the distal end brazed portion 41, the first proximal end brazed portion 42, and the second proximal end brazed portion 43 include an aluminum alloy, silver, gold, zinc, a Sn—Pb alloy, a Sn—Au alloy, a Pb—Ag alloy, and a Sn—Ag alloy. It is preferable that the material be gold, a Sn—Au alloy, or a Sn—Ag alloy. This is because, in this case, the strengths of the distal and proximal end brazed portions described above are increased.

The guidewire 1 according to the present embodiment has the following advantageous effects (1) to (6).

(1) In the guidewire 1 according to the present embodiment, the outer coil 20 and the inner coil 30 respectively include the first bent portion 22 and the second bent portion 32, which are bent in the first direction X. Therefore, the guidewire 1 is a so-called preshaped guidewire, which has high vascular selectivity.

In particular, the guidewire 1 according to the present embodiment has particularly high selectivity in selecting an acute-angle branch vessel. This will be described with reference to FIGS. 2A to 2C.

Figure 2A:
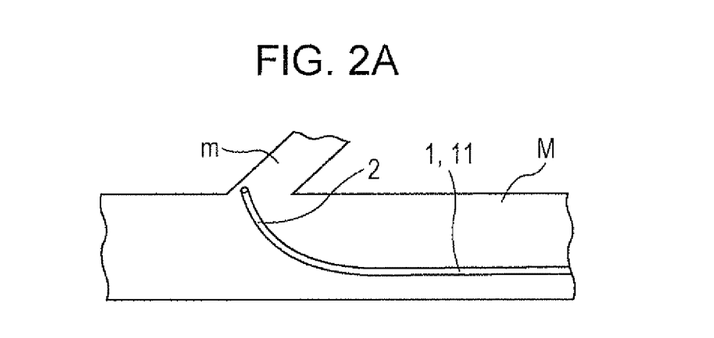
FIGS. 2A to 2C illustrate the guidewire of FIGS. 1A to 1C that is being selectively inserted into an acute-angle branch vessel.
Figure 2B:
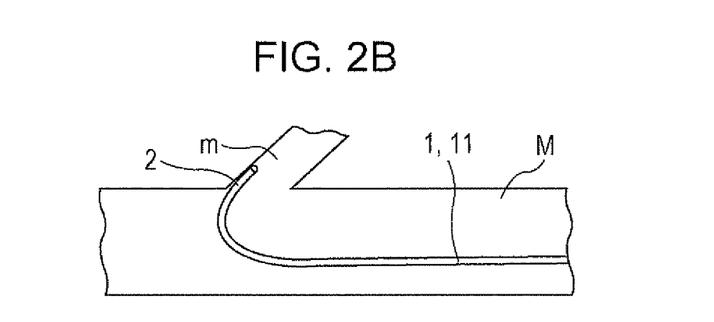
Figure 2C:
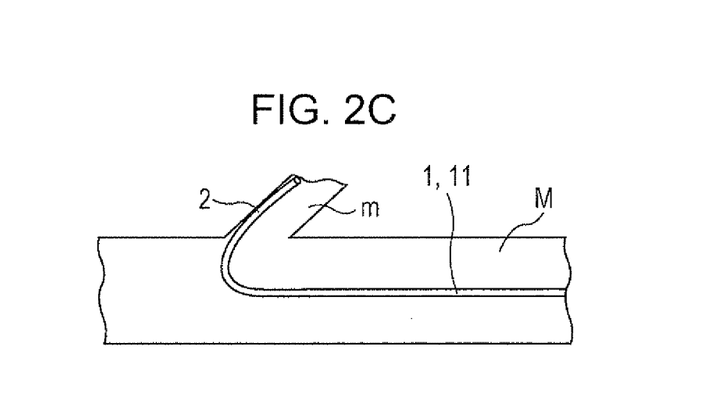

As illustrated in FIG. 2A, the guidewire 1 is inserted into a trunk blood vessel M before the guidewire 1 is inserted into a branch vessel. Then, as illustrated in FIG. 2B, a portion of the distal portion of the guidewire 1 that is on the distal side of the first bent portion and the second bent portion (hereinafter, referred to as a bent end portion 2) is pressed against an inner wall of an acute-angle branch vessel m. Here, the second angle, which is the bending angle of the second bent portion of the inner coil, is larger than the first angle, which is the bending angle of a first bent portion of the outer coil. That is, the inner coil is bent more sharply in the first direction (inward) than the outer coil. Thus, the inner coil can be more easily bent in the first direction (inward) than the outer coil. Therefore, when the bent end portion 2 is, for example, pressed against an inner wall of the acute-angle branch vessel m and a bending force is applied to the bent end portion 2, the bent end portion 2 can be easily bent in accordance with the curvature of the acute-angle branch vessel m. Accordingly, with the guidewire 1 according to the present embodiment, an operator can easily select the acute-angle branch vessel m, although the guidewire 1 does not have a large bending angle. As a result, the operator can smoothly insert the guidewire 1 into the acute-angle branch vessel m by continuing to push the guidewire 1 as illustrated in FIG. 2C. Naturally, an operator can selectively insert the guidewire 1 according to the present embodiment easily into an obtuse-angle branch vessel (not shown), which is an easier target for insertion of the guidewire 1 than an acute-angle branch vessel m.

(2) The guidewire 1 according to the present embodiment includes the fixing unit 40 that fixes the outer coil 20 and the inner coil 30 to each other. The inner coil 30 is fixed to the outer coil 20 through the fixing unit 40 in a state in which the inner coil 30 is urged in the first direction X. Therefore, when the bent end portion 2 is, for example, pressed against an inner wall of a branch vessel and a bending force is applied to the bent end portion 2, the inner coil 30 can be easily bent in the first direction X due to an urging force of the inner coil 30 in the first direction X. As a result, the outer coil 20, which is fixed to the inner coil 30, can be easily bent in the first direction X. Therefore, the bent end portion can be more easily bent in accordance with the curvature of a branch vessel, so that an operator can selectively insert the guidewire into the branch vessel more easily.

(3) In the guidewire 1 according to the present embodiment, the outer coil 20 has a linear shape prior to assembly of the guidewire 1; and the inner coil 30, which is urged in the first direction X, is in contact with the outer coil 20, and thereby the first bent portion 22 is formed. Because the first bent portion 22 is formed not by bending the outer coil 20 beforehand but by using an urging force of the inner coil 30, the guidewire 1 can be manufactured easily at low cost.

(4) In the guidewire 1 according to the present embodiment, the axis $L_i$ of the second distal end section 31 of the inner coil 30, which is located on the distal side of the second bent portion 32, is displaced in the first direction X from the axis $L_o$ of the first distal end section 21 of the outer coil 20, which is located on the distal side of the first bent portion 22. Because the second distal end section 31 of the inner coil 30 is displaced from the first distal end section 21 of the outer coil 20 in the first direction X, the inner coil 30 can be more easily bent in the first direction X. As a result, the guidewire 1 has higher vascular selectivity.

(5) In the guidewire 1 according to the present embodiment, the inner coil 30 is disposed so as to cover the distal end portion 11, and the axis $L_l$ of the distal end portion 11 is displaced from the axis $L_i$ of the second distal end section 31 toward the axis $L_o$ of the first distal end section 21. The distal end portion 11 of the core shaft 10 is displaced from the axis $L_i$ of the second distal end section 31 of the inner coil 30 toward the axis $L_o$ of the first distal end section 21 of the outer coil 20 (that is, the axis of the guidewire 1). Thus, the distal end portion 11 of the core shaft 10, which functions as a rotation axis of the guidewire 1, passes through a position that is nearer to the axis of the guidewire 1. Therefore, when the proximal end portion 12 of the core shaft 10 (a proximal portion of the guidewire 1) is rotated, the distal end portion 11 of the core shaft 10 (the distal portion of the guidewire 1) is easily rotated so as to follow the rotation of the proximal end portion 12, and hence the guidewire 1 has better torque transmission. Because the guidewire 1 has good torque transmission, an operator can selectively insert the distal portion of the guidewire 1 into a target branch vessel easily. Moreover, because the guidewire 1 can be easily bent in the first direction X, the operator can insert the distal portion further into the branch vessel along the curvature of the branch vessel. Therefore, the guidewire has significantly high vascular selectivity.

(6) In the guidewire 1 according to the present embodiment, the inner coil 30 may be a linear cylindrical member that is formed by stranding a plurality of wires and the outer coil 20 may be a linear cylindrical member that is formed by winding a single wire. In this case, the inner coil 30, which includes a plurality of wires, has high rigidity; and the outer coil 20, which includes a single wire, is flexible. Therefore, the outer coil 20 can be easily bent so as to follow the shape of the inner coil 30, which is more sharply bent in the first direction X than the outer coil 20, so that the bent end portion 2 of the guidewire 1 can be easily bent in accordance with the curvature of a branch vessel.

The guidewire according to the present embodiment may be made, for example, through the following steps.

First Assembly Process

Figure 3A:
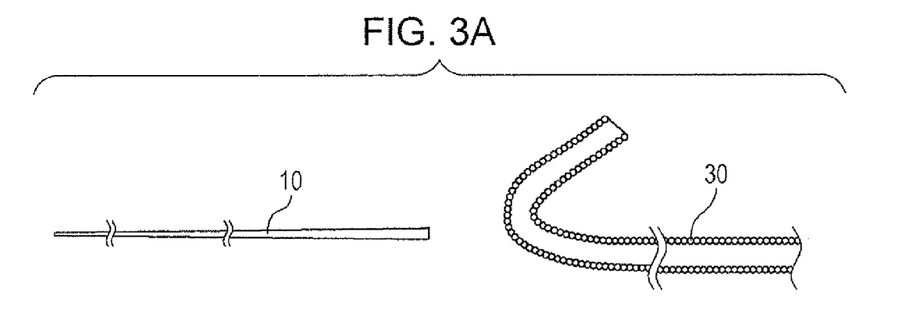
FIGS. 3A to 3C schematically illustrate steps for manufacturing the guidewire illustrated in FIGS. 1A to 1C.

As illustrated in FIG. 3A, a core shaft is prepared. The core shaft is a linear cylindrical member that tapers from a proximal end portion to a distal end portion thereof. An inner coil is prepared. The inner coil has a bent portion that is bent in the first direction at an angle that is larger than the second angle β, which is the bending angle of the inner coil after the guidewire has been made through the subsequent steps.

Figure 3B:
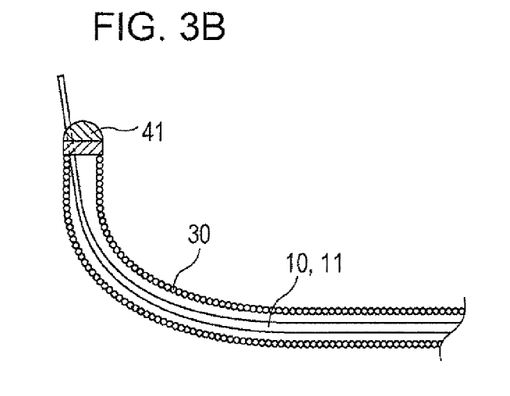

Next, as illustrated in FIG. 3B, a distal end portion of the core shaft is inserted into the inner coil. Then, the distal end portion of the core shaft, which has a linear shape prior to assembly of the guidewire, comes into contact with the inner coil, and the bending angle of the bent portion of the inner coil is slightly reduced. In this state, first brazing is performed. That is, the tip portion of the distal end portion of the core shaft and the tip portion of the second distal end section of the inner coil are fixed to each other through the distal end brazed portion, which has a small diameter. Moreover, the middle portion of the distal end portion of the core shaft and the proximal end of the second proximal end portion of the inner coil are fixed to each other through the second proximal end brazed portion. Thus, a first assembly is made. The bent portion of the first assembly, which corresponds to the second bent portion, has an angle that is larger than the second angle β of the second bent portion of the inner coil of a finished guidewire.

Second Assembly Process

Figure 3C:
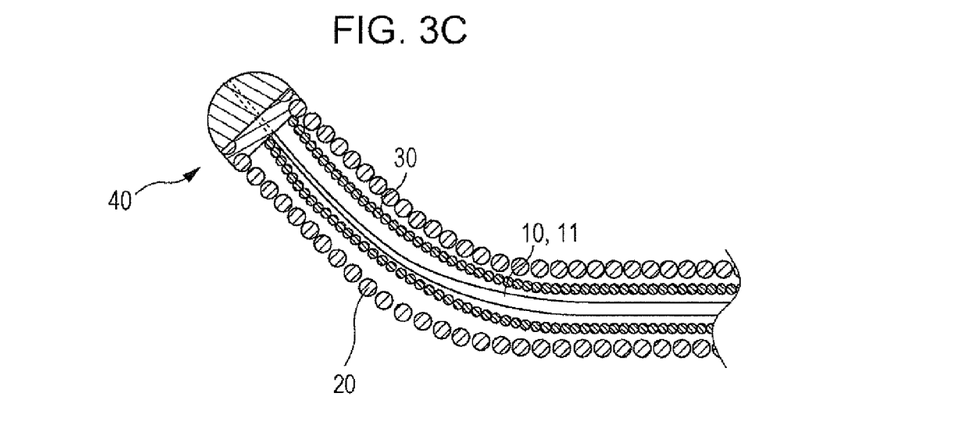

An outer coil is prepared. The outer coil is a linear cylindrical member that is made by helically winding a single wire or by stranding a plurality of wires. As illustrated in FIG. 3C, a distal end portion of the first assembly is inserted into the outer coil. Then, the inner coil of the first assembly, which has been bent, comes into contact with the distal end portion of outer coil, which has a linear shape prior to assembly of the guidewire. As a result, the bending angle of the inner coil is slightly reduced, and the second bent portion having the second angle β is formed. The linear outer coil is bent in the first direction, and the first bent portion having the first angle α is formed. In this state, second brazing is performed. That is, the tip portion of the distal end portion of the core shaft, the tip portion of the second distal end section of the inner coil, and the tip portion of the first distal end section of the outer coil are fixed to one another through the distal end brazed portion, which is hemispherical and has a large diameter. Moreover, a proximal end of the tip portion of the distal end portion of the core shaft and a proximal end of the tip portion of the first proximal end portion of the outer coil are fixed to each other through the first proximal end brazed portion. Through the steps described above, a guidewire according to the present embodiment is made.

Figure 4:
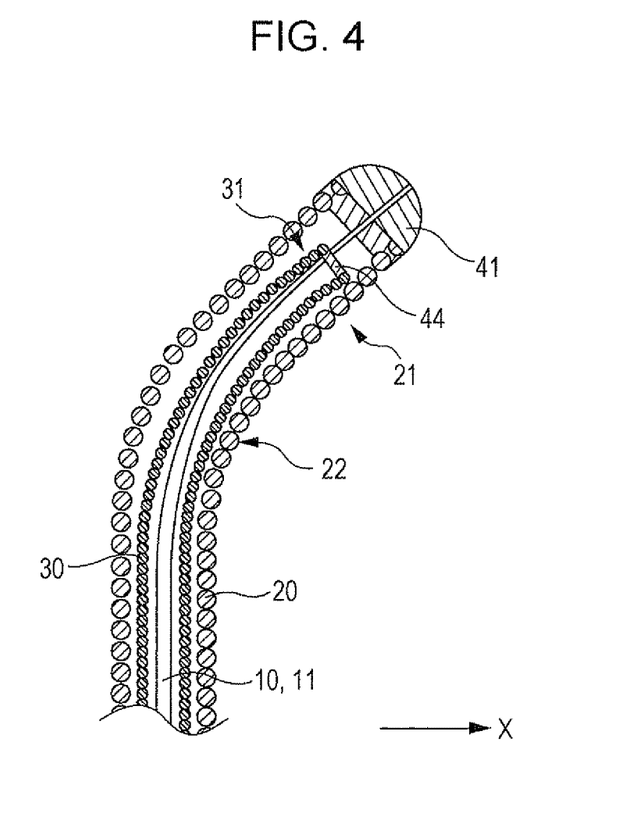
FIG. 4 is an enlarged view of a distal end portion of a guidewire according to a second embodiment of the present invention.

Hereinafter, a guidewire according to a second embodiment of the present invention will be described with reference to the drawings. Except that the outer coil and the inner coil are not fixed to each other through a fixing unit, the guidewire according to the present embodiment has the same structure as the guidewire according to the first embodiment. Description of the structure the same as that of the first embodiment will be omitted.

FIG. 4 is an enlarged view of a distal end portion of a guidewire 1 according to the second embodiment of the present invention. The elements in FIG. 4 and the elements in FIGS. 1A to 1C that are denoted by the same numerals correspond to each other.

As illustrated in FIG. 4, in the guidewire 1 according to the present embodiment, an outer coil 20 and an inner coil 30 are not fixed to each other through a fixing unit.

To be specific, a tip portion of a first distal end section 21 of the outer coil 20 and a tip portion of a distal end portion 11 of the core shaft 10 are fixed to each other through a first distal end brazed portion 41, which is hemispherical. A tip portion of a second distal end section 31 of the inner coil 30 does not reach the first distal end brazed portion 41 and is separated from the first distal end brazed portion 41 toward the proximal end side. The tip portion of the second distal end section 31 of the inner coil 30 and a portion of the core shaft 10 that is separated from the tip portion of the distal end portion 11 toward the proximal end side are fixed to each other through a second distal end brazed portion 44. Here, the tip portion of the second distal end section 31 of the inner coil 30 and the portion of the core shaft 10 that is separated from the tip portion of the distal end portion 11 toward the proximal end side are fixed to each other through the second distal end brazed portion 44 in a state in which the inner coil 30 is urged in a first direction X. The outer coil 20 has a linear shape prior to assembly of the guidewire 1; and the second distal end section 31 of the inner coil 30, which is urged in the first direction X, is in contact with an inner surface of the outer coil 20, and thereby a first bent portion 22 is formed.

The guidewire according to the second embodiment also has the aforementioned advantageous effects (1), (3), (4), (5) and (6) of the first embodiment. Moreover, the guidewire according to the second embodiment has the following advantageous effects (7) and (8).

(7) In the guidewire according to the present embodiment, the tip portion of the second distal end section of the inner coil and the portion of the distal end portion of the core shaft that is separated from the tip portion of the distal end portion toward the proximal end side are fixed to each other through the second distal end brazed portion in a state in which the inner coil is urged in the first direction. Therefore, when the bent end portion for example, pressed against an inner wall of a branch vessel and a bending force is applied to the bent end portion, the inner coil can be easily bent in the first direction due to an urging force of the inner coil in the first direction. As a result, the bent end portion can be more easily bent in accordance with the curvature of a branch vessel, so that an operator can selectively insert the guidewire into the branch vessel more easily.

(8) In the guidewire according to the present embodiment, the tip portion of the second distal end section of the inner coil is separated from the first distal end brazed portion toward the proximal end side and is fixed to a portion of the core shaft that is separated from the tip portion of the distal end portion toward the proximal end side through the second distal end brazed portion. Thus, a spacer section, which includes a part of the first distal end section of the outer coil and a part the distal end portion of the core shaft, is provided between the first distal end brazed portion and the tip portion of the second distal end section of the inner coil. The spacer section, which does not include the inner coil, has high flexibility. Thus, the first distal end brazed portion, which is rigid and has low flexibility; the spacer section, which has high flexibility; and the second distal end brazed portion, which is rigid and has low flexibility, are arranged from the distal portion toward the proximal portion of the guidewire. Therefore, when the distal portion of the guide wire is, for example, pressed against an inner wall of a blood vessel and an external force, such as a bending force, is applied to the distal portion of the guidewire, the distal portion can be easily bent at the spacer section. Accordingly, the guidewire is unlikely to damage the inner wall of the blood vessel, although the guidewire includes rigid distal end brazed portions.

The guidewire according to the present embodiment can be manufactured by using a method the same as that of manufacturing the guidewire according to the first embodiment, except that the tip portion of the second distal end section of the inner coil and a portion of the core shaft that is separated from the tip portion of the distal end portion toward the proximal end side are fixed to each other through the second distal end brazed portion.

In a guidewire according to the present invention, the outer coil may have a linear shape prior to assembly of the guidewire; and the inner coil, which is urged in the first direction, may be in contact with the outer coil, and thereby the first bent portion of the outer coil may be formed. Alternatively, the outer coil may be bent at a predetermined angle in the first direction prior to assembly of the guidewire; and the inner coil, which is urged in the first direction, may be in contact with the outer coil, and thereby the first bent portion of the outer coil may be formed. Further alternatively, the outer coil may be bent at the first angle in the first direction prior to assembly of the guidewire; and the outer coil may be inserted into the inner coil, which is bent at the second angle in the first direction, and thereby the first bent portion of the outer coil may be formed.

In a guidewire according to the present invention, it is preferable that the outer coil include a first distal end section on a distal side of the first bent portion, the inner coil include a second distal end section on a distal side of the second bent portion, and the axis of the second distal end section be displaced from the axis of the first distal end section in the first direction. Alternatively, the axis of the second distal end section may be displaced from the axis of the first distal end section in a direction opposite to the first direction. The axis of the second distal end section may be the same as the axis of the first distal end section.

In a guidewire according to the present invention, as long as the inner coil is disposed inside of the outer coil, the inner coil may be disposed inside of the outer coil so as to cover the distal end portion of the core shaft or the inner coil may be disposed inside of the outer coil so as to be adjacent to the distal end portion of the core shaft. In these cases, it is preferable that the axis of the distal end portion of the core shaft be displaced from the axis of the second distal end section of the inner coil toward the axis of the first distal end section of the outer coil.

What is claimed is:

1. A guidewire comprising:
a core shaft including a distal end portion, a proximal end portion, and a longitudinal axis;
an outer coil disposed radially outward of the distal end portion of the core shaft; and
an inner coil disposed radially inward of the outer coil and radially outward of the distal end portion of the core shaft,
wherein:
the outer coil includes a first bent portion that is bent at a first angle in a first direction,
the inner coil includes a second bent portion that is bent at a second angle in the first direction,
the second bent portion is disposed adjacent to the first bent portion,
a proximal end section of the inner coil is centrally aligned with a proximal end section of the outer coil,
the second angle is larger than the first angle,
the guidewire has a space between an outer peripheral surface of the proximal end section of the inner coil and an inner peripheral surface of the outer coil,
a distal end section of the inner coil directly contacts the inner peripheral surface of the outer coil and the distal end portion of the core shaft, and
a center axis of the distal end portion of the core shaft is displaced from a center axis of the distal end section of the inner coil toward a center axis of a distal end section of the outer coil.

2. The guidewire according to claim 1, further comprising a fixing end that fixes the outer coil to the inner coil so that the inner coil is urged in the first direction.

3. The guidewire according to claim 2, wherein:
the outer coil has a linear shape prior to assembly of the guidewire, and
the inner coil, which is pre-bent so as to be urged in the first direction, is in contact with the outer coil, to thereby form the first bent direction of the outer coil.

4. The guidewire according to claim 1, wherein:
a distal end of the outer coil and a proximal end of the outer coil are fixed to the core shaft,
a distal end of the inner coil and a proximal end of the inner coil are fixed to the core shaft, and
the center axis of the distal end section of the inner coil is displaced to the first direction from the center axis of the distal end section of the outer coil.

5. A guidewire comprising:
a core shaft including a distal end portion, a proximal end portion, and a longitudinal axis;
an outer coil disposed radially outward of the distal end portion of the core shaft; and
an inner coil disposed radially inward of the outer coil and radially outward of the distal end portion of the core shaft,
wherein:
the outer coil includes a first bent portion that is bent at a first angle in a first direction,
the inner coil includes a second bent portion that is bent at a second angle in the first direction,
the second bent portion is disposed adjacent to the first bent portion,
a proximal end section of the inner coil is centrally aligned with a proximal end section of the outer coil and the proximal end portion of the core shaft,
the second angle is larger than the first angle, the guidewire has a space between an outer peripheral surface of the proximal end section of the inner coil and an inner peripheral surface of the outer coil, and
a distal end section of the inner coil directly contacts the inner peripheral surface of the outer coil and the distal end portion of the core shaft.

\* \* \* \* \*